US010802018B2

(12) United States Patent
Cubukcu et al.

(10) Patent No.: US 10,802,018 B2
(45) Date of Patent: Oct. 13, 2020

(54) MULTIMODAL BIOSENSOR

(71) Applicant: The Trustees of the University of Pennsylvania, Philadelphia, PA (US)

(72) Inventors: Ertugrul Cubukcu, Ardmore, PA (US); Alexander Yutong Zhu, Cambridge, MA (US); Fei Yi, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 543 days.

(21) Appl. No.: 14/932,373

(22) Filed: Nov. 4, 2015

(65) Prior Publication Data

US 2016/0123973 A1    May 5, 2016

Related U.S. Application Data

(60) Provisional application No. 62/074,889, filed on Nov. 4, 2014.

(51) Int. Cl.
| | | |
|---|---|---|
| *G01N 33/543* | (2006.01) | |
| *G01N 27/414* | (2006.01) | |
| *G01N 29/02* | (2006.01) | |
| *H01L 29/16* | (2006.01) | |
| *G01N 29/036* | (2006.01) | |
| *G01N 21/552* | (2014.01) | |
| *H01L 29/786* | (2006.01) | |

(52) U.S. Cl.
CPC ..... *G01N 33/54373* (2013.01); *G01N 21/554* (2013.01); *G01N 27/4145* (2013.01); *G01N 29/022* (2013.01); *G01N 29/036* (2013.01); *H01L 29/1606* (2013.01); *H01L 29/78684* (2013.01); *G01N 2291/0256* (2013.01)

(58) Field of Classification Search
CPC ......... G01N 33/54373; G01N 21/554; G01N 27/4145; G01N 29/022; G01N 29/036; G01N 2291/0256; H01L 29/1606; H01L 29/78684
See application file for complete search history.

(56) References Cited

U.S. PATENT DOCUMENTS

| | | |
|---|---|---|
| 6,914,279 B2 | 7/2005 | Lu |
| 2011/0257033 A1 | 10/2011 | Strano |
| 2014/0103298 A1 | 4/2014 | Lee |

OTHER PUBLICATIONS

Lee, Seung-Woo, et al. "Highly sensitive biosensing using arrays of plasmonic Au nanodisks realized by nanoimprint lithography." ACS nano 5.2 (2011): 897-904.*
Waggoner, Philip S., and Harold G. Craighead. "Micro-and nanomechanical sensors for environmental, chemical, and biological detection." Lab on a Chip 7.10 (2007): 1238-1255.*
Dankerl, Markus, et al. "Graphene Solution-Gated Field-Effect Transistor Array for Sensing Applications." Advanced Functional Materials 20.18 (2010): 3117-3124.*

(Continued)

*Primary Examiner* — Robert J Eom
(74) *Attorney, Agent, or Firm* — BakerHostetler

(57) ABSTRACT

Multimodal biosensor devices are disclosed. A device may include at least two sensors selected from: (i) a nanomechanical resonator; (ii) plasmonic nanodisk antennae; and (iii) a field effect transistor. The biosensor device is capable of transducing the adsorption of biomolecules onto the biosensor device into optical, electrical and/or mechanical signals.

18 Claims, 4 Drawing Sheets

(56) References Cited

OTHER PUBLICATIONS

Schumacher, Thorsten, et al. "Nanoantenna-enhanced ultrafast nonlinear spectroscopy of a single gold nanoparticle." Nature communications 2 (2011): 333.*

Nakazato, Kazuo. "An integrated ISFET sensor array." Sensors 9.11 (2009): 8831-8851.*

Guo, Q., et al., "Silicon-on-glass graphene-functionalized leaky cavity mode nanophotonic biosensor," 2013, pp. A-G, ACS Photonics.

Yi, F., et al., "Plasmonically enhanced thermomechanical detection of infrared radiation," Mar. 13, 2013, pp. 1638-1643, vol. 13, Nano Letters, ACS Publications.

Zhu, A.Y., et al., "Optoelectromechanical multimodal biosensor with graphene active region," Sep. 2, 2014, pp. A-I, Nano Letters, ACS Publications.

* cited by examiner

MULTIMODAL BIOSENSOR

CROSS-REFERENCE TO RELATED APPLICATIONS

This application claims the benefit of priority of U.S. Provisional Application No. 62/074,889, filed Nov. 4, 2014, the contents of which are incorporated by reference herein, in their entireties and for all purposes.

STATEMENT REGARDING FEDERALLY SPONSORED RESEARCH

This invention was made with government support under grant number IIP1312202 and ECCS1408139 awarded by the National Science Foundation. The government has certain rights in the invention.

FIELD OF THE INVENTION

The present invention relates to a multimodal biosensor that is capable of transducing the adsorption of biomolecules into optical, electrical and/or mechanical signals.

BACKGROUND OF THE INVENTION

Recent developments in nanotechnology have led to unprecedented advances, both in terms of improving existing device performance and establishing novel functionalities. Within the context of bioanalytics, nanosensors based on plasmonic nanostructures, nanomechanical cantilevers, carbon nanotubes, semiconductor nanowires, and graphene have been shown to possess high sensitivities down to the single molecular limit, a high spatial resolution for extremely localized detection, and a relatively fast analysis time. This has given rise to the possibility of rapid and potentially low-cost point-of-care diagnostics for medical screening, among other applications.

Existing sensing platforms are predominantly single-mode devices that transduce only one type of signal through specific molecular conjugation. In this case, the sensor surface is functionalized with the appropriate binding molecules which preferentially bind to the target analyte, causing a change in the functional property of the device. In addition to serving as a binary valued test for the presence of these molecules, the magnitude of the functional property change can also be used to determine their concentration. However, this single-mode sensing approach has some major limitations. First, it is subject to a necessary trade-off between molecular sensitivity and (linear) dynamic range. The latter is fundamentally constrained by the ratio of perturbative to original sensor response, which must be large in order to provide a high sensitivity, which in turn lowers the saturation limit. As a result, the effective sensor operation range for single mode sensors is typically only two to three orders of magnitude of the target protein concentration. Furthermore, the adsorption of biochemical molecules is quintessentially a multiphysics process that simultaneously generates localized perturbations in mass, dielectric permittivity, and electrical conductance, to name a few commonly measured quantities. By definition, single mode devices are only able to capture information about a single property. Thus, there remains a need for biosensors that have greater functionality, and that are capable of detecting different adsorbed biomolecules with higher sensitivity and specificity.

SUMMARY OF THE INVENTION

An embodiment of the present invention relates to a multimodal biosensor device comprising at least two sensors selected from:
(i) a nanomechanical resonator;
(ii) plasmonic nanodisk antennae; and
(iii) a field effect transistor,
wherein the biosensor device is capable of transducing the adsorption of biomolecules onto the biosensor device into at least two signals selected from optical, electrical and mechanical signals.

Another embodiment of the present invention relates to a method of using a multimodal biosensor device comprising adsorbing biomolecules (e.g., proteins, peptides, DNA or RNA) onto the multimodal biosensor device,
wherein the multimodal biosensor device transduces the adsorption of the biomolecules into at least two signals selected from optical, electrical and mechanical, wherein the multimodal biosensor device comprises at least two sensors selected from:
(i) a nanomechanical resonator;
(ii) plasmonic nanodisk antennae; and
(iii) a field effect transistor.

Another embodiment of the present invention relates to a method of making a multimodal biosensor device comprising depositing plasmonic nanodisk antennae and a field effect transistor on a nanomechanical resonator.

DETAILED DESCRIPTION OF THE INVENTION

Figure 1:
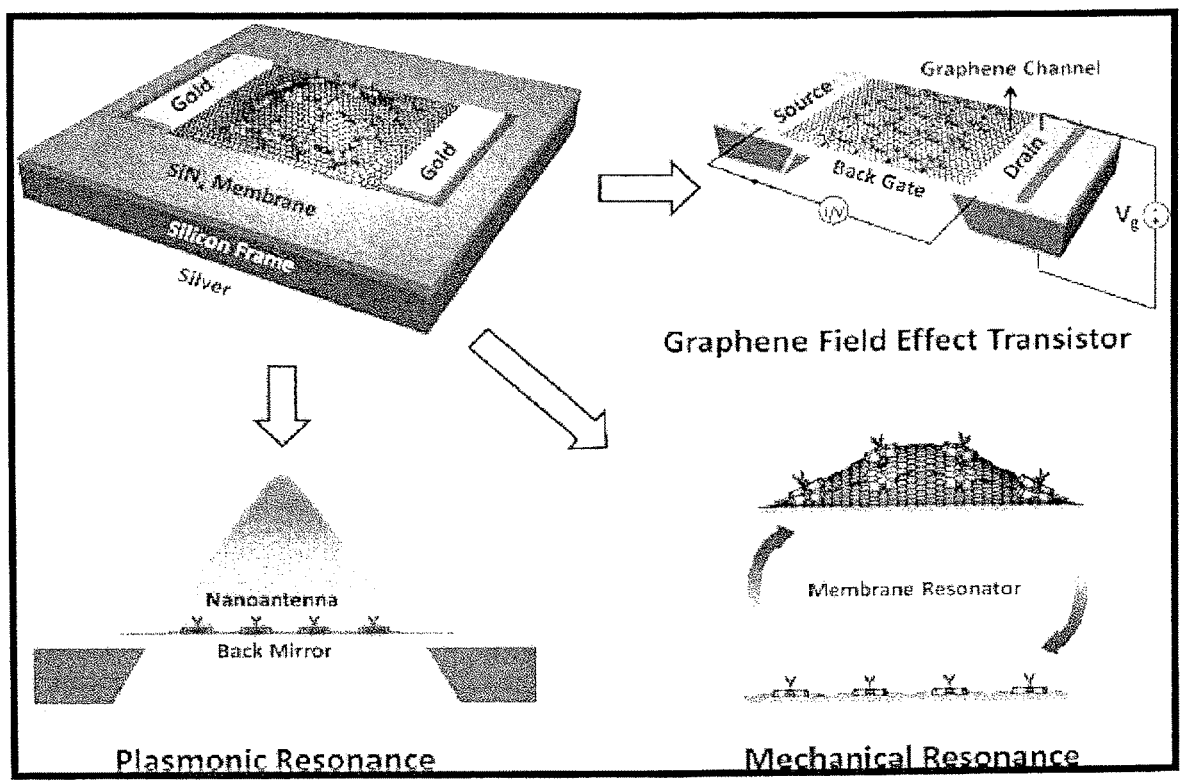
FIG. 1 is a schematic representation of an embodiment of a device structure, in accordance with aspects of the present invention, including an angled top view of a device comprising a freestanding silicon nitride membrane suspended over an etched silicon frame; and plasmonic nanodisk antennae, top electrodes, a silver backgate, and graphene, which were deposited onto the silicon nitride membrane.

A nanoscale sensing device with optical, electronic and mechanical functional elements integrated on the same device is described below. Although a three-mode sensor is described, it is contemplated that more or fewer modes may be incorporated into the device.

Most single-mode sensors in the prior art have a tradeoff between sensitivity (the lower detection limit) and dynamic range (the difference between the lowest and greatest concentrations that the sensor can detect). By using three sensing modes, embodiments of the present invention were demonstrated to have a dynamic range of five orders of magnitude of protein concentration, an improvement over existing single mode sensors by two to three orders of magnitude. The individual linear dynamic range is about 0.5 pM to about 1 nM for the mechanical sensing mode and about 30 pM to about 30 nM for both electrical and optical modes, yielding a combined linear dynamic range from subpicomolar to tens of nanomolar. The combination of low detection limit, large dynamic range, and discrimination provided by the three sensing modes give sensors of the present invention several advantages over the existing state of the art.

By having each element target a different concentration regime, the sensitivity-dynamic range trade-off of traditional single mode sensors can be significantly mitigated. Furthermore, the synergistic operation of the sensing modes enables one to monitor and characterize adsorption events in the full optoelectromechanical parameter space. Multiple key parameters intrinsic to the adsorbed molecules, such as mass, surface dissociation constant, binding affinity, and characteristic optical or electrical surface sensitivities can thus be obtained from the individual characterization curves on a single device. This greatly expanded functionality may enable the detection and differentiation of multiple protein molecules, through the use of appropriate target-receptor molecules.

Most sensors only act on one mode to detect the presence of an analyte; however, embodiments of the present invention use at least two modes, namely, optical (plasmonic), mechanical, and/or electrical, and preferably all three. The presence of a molecule on the sensor will affect the device's mechanical resonance, electrical conductance, and plasmonic response. Thus, a sensor measurement for a given molecule can be taken using three independent modes. This allows much greater discrimination than the prior art, because it is unlikely that any two given molecules will produce the same response in three separate, independent modes.

According to an embodiment of the present invention, a multimodal biosensor device comprises at least two sensors selected from: (i) a nanomechanical resonator for sensing mechanical signals; (ii) plasmonic nanodisk antennae (e.g., gold nanodisk antennae), preferably disposed on a top surface of the nanomechanical resonator, for sensing optical (plasmonic) signals; and (iii) a field effect transistor (e.g., graphene or silicon), preferably disposed on a top surface of the nanomechanical resonator, for sensing electrical signals. The biosensor device is capable of transducing the adsorption of biomolecules onto the biosensor device into at least two signals selected from optical, electrical and mechanical. In many cases, the signals are transduced simultaneously. According to particular embodiments, the device includes all three sensors (i.e., a nanomechanical resonator, plasmonic nanodisk antennae and a field effect transistor).

Alternatively, the device includes any two of the three sensors. For example, the device may include the plasmonic nanodisk antennae disposed on the nanomechanical resonator, but no field effect transistor. As another example, the device may include the field effect transistor disposed on the nanomechanical resonator, but no plasmonic nanodisk antennae. As another example, the device may include the plasmonic nanodisk antennae and the field effect transistor, but no nanomechanical resonator (in this embodiment, the device may include a layer of silicon dioxide as a substrate, instead of the nanomechanical resonator).

According to another embodiment, the device includes one or more additional sensors (e.g., the device further comprises an electrochemical sensor in addition to the at least two selected from nanomechanical resonator, plasmonic nanodisk antennae and field effect transistor). According to particular embodiments, the biosensor does not include any ZnO nanostructures (e.g., ZnO nanotips).

According to particular embodiments, the nanomechanical resonator may function as a substrate for other components of the device (e.g., it may be a "nanomechanical resonator substrate" wherein plasmonic nanodisk antennae and/or a field effect transistor are disposed on the nanomechanical resonator substrate). Alternatively, the nanomechanical resonator does not function as a substrate for other components of the device (e.g., a layer of silicon dioxide functions as a substrate instead).

The nanomechanical resonator may comprise a silicon nitride membrane, which may be coupled to a silicon frame. According to this embodiment, the nanomechanical resonator preferably functions as a substrate for other components of the device. The silicon frame may include a metal layer (e.g., silver) on its underside (i.e., on the surface that is opposite its top surface). The thickness of the metal layer may be between about 50 nm and about 200 nm, e.g., between about 75 nm and about 175 nm, between about 100 nm and about 150 nm, or about 100 nm.

A free standing silicon nitride membrane is a nanomechanical resonator that is very sensitive to any small variation in the mass. Therefore, the mass of the biomolecules adsorbed to the membrane can be measured through the frequency shifts in the mechanical resonances. An array of plasmonic nanodisk antennae may be fabricated on top of the membrane. In certain embodiments, the nanodisks together with a silver mirror deposited on the underside of the membrane support a strongly localized surface plasmon resonance which is an accurate readout of the perturbed optical index change at the surface by the adsorbed biomolecules. In order to electrically read out the adsorbed biomolecules, a field effect transistor (preferably graphene-based) may be embedded in the nitride window. By monitoring the change in the charge neutrality condition of the graphene channel, one can measure the amount of biomolecules which act as electron donors or acceptors. Thus, the nanomechanical resonator (e.g., silicon nitride membrane) produces mechanical signals, the plasmonic nanodisk antennae (e.g., gold nanodisk antennae) produce optical (plasmonic) signals, and the field effect transistor (e.g., graphene monolayer) produces electrical signals.

According to an embodiment of the present invention, the device (FIG. 1) comprises a freestanding low stress silicon nitride membrane clamped on all sides to a silicon frame, a configuration capable of supporting high quality (Q) factor mechanical resonance modes which are highly sensitive to adsorbed mass. It also serves as a structural support for the subsequent introduction of plasmonically active gold nanodisk antennae and graphene monolayer transferred onto the top surface. The nanoantennae enable surface refractive index sensing via their spectrally resonant electromagnetic near-fields, while the graphene acts as a traditional field effect transistor (FET) sensing channel and bioactive interface for biomolecule (e.g., protein, peptide and/or nucleic acid) adsorption. In this embodiment, a thin metal coating (e.g., about 50 nm, 100 nm, 150 nm, or 200 nm) on the underside of the membrane serves as the gate electrode (with the membrane itself as the gate dielectric). Electrical sensing is accomplished by standard operation of the device as a graphene FET. The three subsequent modes of operation are shown: plasmonic resonance sensing via standard optical spectroscopy, detection of doping levels in the graphene FET channel by I-V gating, and mass sensing by probing the resonance position of the fundamental membrane mechanical resonance mode. All three modes of operation can be achieved on the same device platform.

Another embodiment of the present invention provides a method of using a multimodal biosensor device comprising adsorbing biomolecules (e.g., peptides, proteins, or nucleic acids such as DNA or RNA) onto the multimodal biosensor device, wherein the multimodal biosensor device transduces the adsorption of the biomolecules into at least two (or all three) of optical, electrical and mechanical signals. According to alternative embodiments, the multimodal biosensor may include more than three sensors (e.g., the device may further comprise an electrochemical sensor), and may therefore be used to transduce the adsorption of biomolecules into more than three signals (e.g., optical, electrical, mechanical and electrochemical signals). The biosensors of the present invention may be used, for example, to detect harmful chemicals (e.g., to screen for chemical or biological warfare agents), or to perform medical diagnostics (e.g., to measure molecules in biological fluids, such as dopamine or cortisol in human sweat).

Another embodiment of the present invention provides a method of making a multimodal biosensor device comprising depositing plasmonic nanodisk antennae (e.g., gold nanodisk antennae) and a field effect transistor (e.g., graphene) on a top surface of a nanomechanical resonator (e.g., a silicon nitride membrane). The method may further comprise depositing a metal (e.g., silver) onto an underside of the nanomechanical resonator (i.e., the surface of the nanomechanical resonator that is opposite the top surface).

The method may comprise, in accordance with particular aspects of the invention:
  depositing and subsequent back-etching of the silicon nitride to provide a freestanding membrane on a silicon frame (or providing a silicon nitride membrane that has been deposited on a silicon frame, which is commercially available);
  depositing the gold nanodisk antennae, surface source electrodes, and drain electrodes on the silicon nitride membrane by spin-coating a polymethyl methacrylate (PMMA) 495/950 resist bilayer followed by electron beam lithography;
  depositing Ti/Au on the silicon nitride membrane using an electron beam evaporator;
  depositing silver (Ag) on an underside of the silicon nitride membrane to form a gate electrode;
  spin-coating and baking graphene on copper foils with polymethyl methacrylate (PMMA); and
  transferring the graphene on copper foils with PMMA (after etching and removal of underlying copper) onto a field effect transistor channel region of the silicon nitride membrane.

As demonstrated in the Examples below, the applicants have demonstrated a multimodal biosensing device capable of transducing protein binding events into optical, electrical, and mechanical signals. Embodiments of the device have been found to possess detection limits comparable to its single mode counterparts for specific conjugation and exhibit a large linear dynamic sensing range. The device may also be used to differentiate and identify multiple distinct biomolecules (e.g., peptides, proteins, or nucleic acids such as DNA or RNA).

The embodiments of the invention are described above using the term "comprising" and variations thereof. However, it is the intent of the inventors that the term "comprising" may be substituted in any of the embodiments described herein with "consisting of" and "consisting essentially of" without departing from the scope of the invention. Unless specified otherwise, all values provided herein include up to and including the starting points and end points given.

The following examples further illustrate embodiments of the invention and are to be construed as illustrative and not in limitation thereof.

Examples

Sensor Fabrication

Low-stress low pressure chemical vapor deposition (LP-CVD) deposited silicon nitride membranes (100 nm thickness) on silicon with a pre-etched window of 500 µm×500 µm were purchased (Norcada, Inc.). These were subsequently cleaned by oxygen plasma. Periodic disk nanoantenna (diameter, 130 nm; period, 210 nm) and surface source and drain electrodes were introduced by spin-coating a polymethyl methacrylate (PMMA) 495/950 resist bilayer, followed by electron beam lithography (Elionix ELS-7500EX). Ti/Au (3/30 nm) were subsequently deposited using an electron beam evaporator (Kurt Lesker PVD-75). Liftoff was performed at 75° C. in >99% n-methyl pyrrolidinone bath (e.g., Microposit® Remover PG), followed by isopropyl alcohol (IPA) and deionized (DI) water rinse. Fifty nanometers of Ag was deposited on the underside of the device to form the gate electrode. Ag was used instead of a more inert metal such as gold due to the latter's interband transitions in the 630 nm wavelength regime. Samples were stored under vacuum conditions at all times except during optical and electrical testing, and protein additions. To allay concerns about possible sulfidation effects, an additional 20 nm of Au was deposited for the final batch of samples (used for the IgG/Cyt C distinguishing tests) as a passivation layer; identical results to within experimental error were obtained.

Chemical vapor deposition (CVD) graphene on copper foils was purchased from Graphene Supermarket, and mechanically trimmed to desired sizes of greater than the eventual FET channel width. They were then spin-coated with PMMA 495 and baked to maintain structural integrity after etching. Etching was done using Transene APS 100 solution (active ingredient: ammonium peroxodisulfate) for relatively clean etching of copper to remove the underlying copper film, thereby realizing freestanding graphene layers. The graphene/PMMA pieces were mechanically transferred to the field effect transistor (FET) channel region of the devices; these are subsequently baked at 150° C., repeatedly rinsed in acetone/IPA and held for a prolonged period at 200° C. for 30 minutes for resist stripping and residue removal. The measured low doping levels of ~$10^{11}$ cm$^{-2}$ and Raman spectrum suggest relatively clean and defect free graphene was obtained as-transferred.

Protein Preparation and Addition.

Murine (mouse) antibody IgG and its binding conjugate A/G were purchased (Pierce) and sequentially diluted to desired concentrations in standard phosphate-buffered saline solution (PBS buffer). Protein A/G is a recombinant fusion protein that combines IgG binding domains of both Protein A and Protein G. Protein A/G contains four Fc binding domains from Protein A and two from Protein G. Concentrations used were 0.01 and 0.1 M, respectively, to keep each protein in the same chemical environment as their respective native (stock) conditions. Oxidized Cyt C from equine heart (Sigma-Aldrich) was prepared as-received in a similar manner in 0.01 M PBS. Protein additions were accomplished by spotting; 2 µL of solution is withdrawn and spotted on the active area of the device by micropipette, and the drop is then incubated in protected, environmental hood conditions. Typical incubation times are 1.5 h. Samples are then washed in a fresh PBS solution followed by DI water in order to remove excess protein and PBS.

Measurement and Characterization.

Optical measurements were performed using a home-built microscopy setup. A fiber coupled broadband white light source (OceanOptics LS-1) was collimated and focused onto the active area of the sample with a 50× objective (Mitutoyo, 0.42 NA). The reflected light is passed back through the objective and a beam splitter and was imaged by a tube lens (Mitutoyo) and focused by a 10× objective (Olympus, 0.25 NA) into a fiber-coupled charge coupled device (CCD) spectrometer (ThorLabs CCS). All optical spectra taken were referenced against the unpatterned region of the membrane devices; actual power values were obtained by normalizing against source power reflected from a broadband dichroic mirror (ThorLabs). Measurements were identically sampled with a 10 ms exposure time and 10× spectral averaging and identically treated with a 50× boxcar smoothing algorithm. For electrical measurements, samples were reversibly mounted onto a copper-plated chip for easier access to the silver gate electrode. Contacts were made at previously electron-beam deposited source, drain, and gate electrodes using standard micromanipulator controlled gold probe tips. Voltage sweeps were performed by two series connected source-meters (Keithley 2400) at constant source-drain voltage of 100 mV, a step size of 10 mV and a time interval of 5 s/step to allow for hysteresis effects. Data collection was done using a standard LabView software package. Contact and electrode resistances were determined separately through the symmetry of the electrode design and accounted for in final data processing. Mass measurements were taken by mounting the samples using adhesive polydimethylsiloxane (PDMS) gel strips to a piezo-actuated stage in an evacuated chamber. A standard fiber-optic laser interferometry setup, based on the Fabry-Perot cavity formed between the facet of a cleaved fiber and the reflective backplate of the sample, was used to optically determine membrane deflections. A low noise 1550 nm laser was coupled into the fiber through a circulator; the reflected light was routed to a small area PIN diode and the resultant electrical signal sent through a lock-in amplifier (Stanford Research Systems) and RF spectrum analyzer (HP 8565).

To obtain a better physical understanding for each of the sensing modalities, the dependence of each functional property on the amount of adsorbate was identified. For mass sensing, the resonant frequencies of a thin rectangular membrane may in general be written $f_{i,j}=[(i^2+j^2)/2]^{1/2}f_{1,1}$ where i,j are integer mode indices indicating the number of antinodes for the two in-plane dimensions, and $f_{1,1}=(1/2\pi)(k/\beta_{1,1}m)^{1/2}$ is the fundamental resonance mode. k and β are constants related to the membrane spring constant and mode modifiers to the mass; the latter arises because not all added mass contributes equally to the resonant frequency of the membrane, depending on the mode profile of the particular chosen resonance. Then any small changes to membrane mass causes perturbations to frequency of the form $$\Delta f \propto -\frac{\Delta m}{m_\Omega^{3/2}} \propto -Q\frac{\Delta m}{m_\Omega^2} \quad (1)$$

(Equation 1) where $m_\Omega$ is the original mass of the membrane oscillator, Δm is the added mass, and $Q=[(mk)^{1/2}/D]$ (D being the damping coefficient) is the mechanical quality factor of the membrane, which describes the ratio between stored and dissipated power in the system. A resonator with a low initial starting mass and low loss (high Q factor) is desired. Experimental characterization of an embodiment of the device before analyte addition demonstrates a fundamental mode resonance with Q of about $10^4$ (FIG. 2a), a value that is broadly comparable to specialized high Q on-chip micromechanical resonators.

Similarly, graphene is used as the active material for electrical-based sensing mode in an embodiment of the device, due to its high carrier mobility and surface-to-volume ratio (being a two-dimensional material), low electrical noise (in the case of defect-free crystals), as well as low initial carrier concentration. In addition, its relative ease of large-scale preparation via chemical vapor deposition (CVD) and ability to be transferred onto most substrates affords it unique advantages over the aforementioned nanowires. Because of the unique band-structure of graphene, the Fermi energy is directly related to the square root of its carrier concentration n via $EF=h|v_F|(\pi n)^{1/2}$. The latter quantity can be significantly changed by surface adsorbates, via either direct-charge transfer or electrostatic double layer gating effects, which forms the basis for various graphene FET type sensors of the prior art. Here, the applicants adopted a different approach to track the position of the Fermi level itself with varying levels of adsorbate (where Δn is the differential change in carrier concentration)

$$\Delta E_F \propto |v_F|\frac{\Delta n}{\sqrt{n}} \quad (2)$$

(Equation 2) by performing consecutive I-V sweeps of the device at different adsorbate concentrations, and quantifying the change in the minimum conductivity as a function of applied gate voltage, which arises when the number of injected carriers exactly balance the intrinsic and adsorbate-induced doping levels of the graphene (i.e., where the Fermi energy rests at the Dirac point, also termed the charge neutrality point or CNP). Characterization results of the devices indicate high quality graphene crystals with a CNP of 1 V, corresponding to an excess electron concentration of about $10^{11}/cm^2$.

Finally, subwavelength metallic nanostructures are known to support localized surface plasmon resonances due to the collective oscillations of the electron plasma coupled to light. For discrete nanosized particles, the electron oscillation is confined to the particles (i.e., localized). The strong confinement of these electromagnetic modes near the nanoantenna results in significantly enhanced optical near field intensities. These optical resonances depend strongly on the refractive index of the surrounding dielectric medium. Together, these properties form the basis for plasmonic sensing by detecting the perturbations to the surface refractive index or dielectric permittivity due to the adsorbates, which can be measured by determining the optical resonant frequencies of scattering or extinction. Intuitively, in the quasi-static limit (where particle size is much less than incident wavelength) and assuming a simple Drude model for the noble metal, the resonant frequency change can be written $$\Delta\lambda_{max} \propto \lambda_p \frac{2n_d}{\sqrt{2n_d^2+1}} \Delta n_d \quad (3)$$

Figure 2:
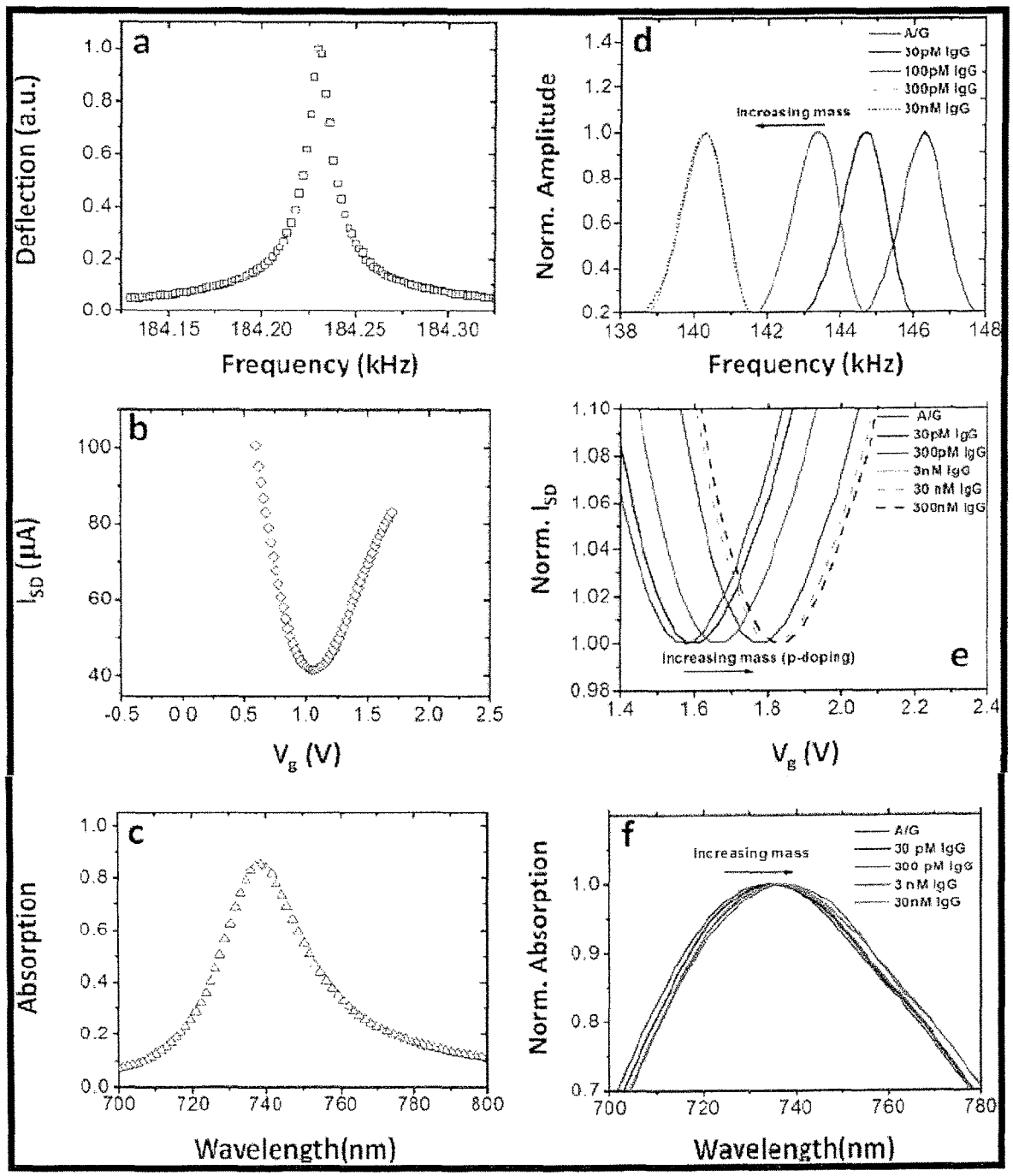
FIG. 2 illustrates mechanical (a), electrical (b), and optical responses (c) of a device sample in accordance with aspects of the present invention; and sensor responses in response to protein binding of the fundamental mechanical resonance mode (d), graphene FET source-drain current-voltage characterization (e), and localized surface plasmon resonance of Au nanodisks (f). Data for each particular concentration were obtained from the same protein addition on the same sample, illustrating signal transduction using all three independent sensing modes.

(Equation 3) where $\lambda p$ is the wavelength corresponding to the (bulk) plasma frequency of the metal nanostructures and $n_d$ is the refractive index of the surrounding dielectric medium. The $\Delta n_d$ term here is a simplfication: it represents the spatially averaged change in permittivity due to the adsorbates, but strictly this is only true for the sensor surface as the bulk medium remains the same. Rigorously $\Delta n_d$ therefore contains terms that quantify the degree of electric field overlap with the adsorbates at the surface; sensitivity thus depends very much on the geometry, size, and chosen material for the plasmonic structures. In addition, a commonly used figure of merit for plasmonic sensors divides the peak wavelength sensitivity ($d\lambda/d_n$) by the full width at half-maximum (fwhm) of the plasmonic resonance peak (or equivalently multiplying by optical Q factor), because the latter determines the minimum detectable change in peak wavelength shift. In an embodiment of the device, the applicants were able to observe a surface plasmon resonance enhanced near-unity absorption due to the coupled nanoantennae-optical cavity configuration with a relatively high optical Q of about 25 (FIG. 2c).

From the previous analysis, it can be seen that this device architecture also exploits multiple synergies: besides the silicon nitride membrane that doubles as a high Q mechanical resonator and relatively high-k gate dielectric, the silver gate electrode also functions as a back reflector to the plasmonic nanoantennae, whose resonance lie at approximately 740 nm. This suppression of optical transmission results in a cavity enhanced resonance peak, increasing optical Q, and sensitivity. This can be understood intuitively as the optical cavity configuration suppresses the outgoing reflected waves via destructive interference and greatly increases the number of round trips made by incident light, resulting in larger absorption, longer confinement time (as well as photon lifetime in the structure) and field intensity at the surface (for an approximately quarter-wavelength cavity the field antinode is at the surface, as is the case here). Lastly, in addition to functioning as a FET sensor, graphene also significantly increases the surface (bio)molecular adsorption limit in general due to a large specific surface area, high polarizability relative to dielectric substrates, and π-π interactions with hydrocarbon chains in biomolecules. Moreover, due to its atomically thin nature it does so without significantly perturbing the optical and mechanical detection modes, thus greatly enhancing their net sensitivities and enabling multicomponent integration.

The applicants first characterized device performance for traditional specific target-receptor type conjugation to ensure that the integration process does not significantly compromise the individual functionality of each sensing channel. Label-free end-point protein detection trials were carried out using murine immunoglobulin G (IgG) with recombinant protein A/G as the specific binding intermediary. In these experiments, the sensor surface is first saturated with the binding protein in order to measure the sensor response (of each mode) that arises from the specific binding of the IgG antibody at various concentrations. The sensor responses are separately monitored across the different modes after an incubation time of 1.5 h for each concentration level. For the mechanical mode, the fundamental resonance frequency linearly shifts to lower values as the protein concentration is increased in the approximately 10 pM range, which is in agreement with Equation 1 (FIG. 3a). A linear fit to the mechanical frequency response in this range leads to a sensitivity of 23.7 Hz/pM with a minimum noise-limited detectable concentration of approximately 0.5 pM. The integrated nanoelectronic sensing response of the graphene FET is characterized by measuring the current voltage (I-V) characteristics of the device for various concentrations of IgG. The I-V curve exhibits a zero-slope feature corresponding to the charge neutrality point of the graphene channel (FIG. 3b). Monitoring the shift in the Fermi level in the electrical measurements allows the applicants to quantify the amount of adsorbed protein and the corresponding concentration for the given incubation time. Although the electrical measurements are performed on the same device following mechanical characterization, there was no observable change in the electrical response for concentrations less than approximately 30 pM, which is limited by the electrical noise. For detectable concentrations, the electrical response is also linear as predicted by Equation 2, yielding a sensitivity of 0.43 V/nM. Finally, optical measurements are performed by illuminating the active device area at normal incidence, exciting the spectrally resonant modes of the nanoantennae. Adsorption of biomolecules causes a change in the local refractive index, causing a shift in the position of the plasmon resonance peak that can in turn be related to the added concentration, as in Equation 3. For optical measurements, the initial sensitivity of the device is found to be 12.1 nm/nM, which translates to an instrument-limited minimum detection limit of approximately 30 pM as well (FIG. 3c).

Figure 3:
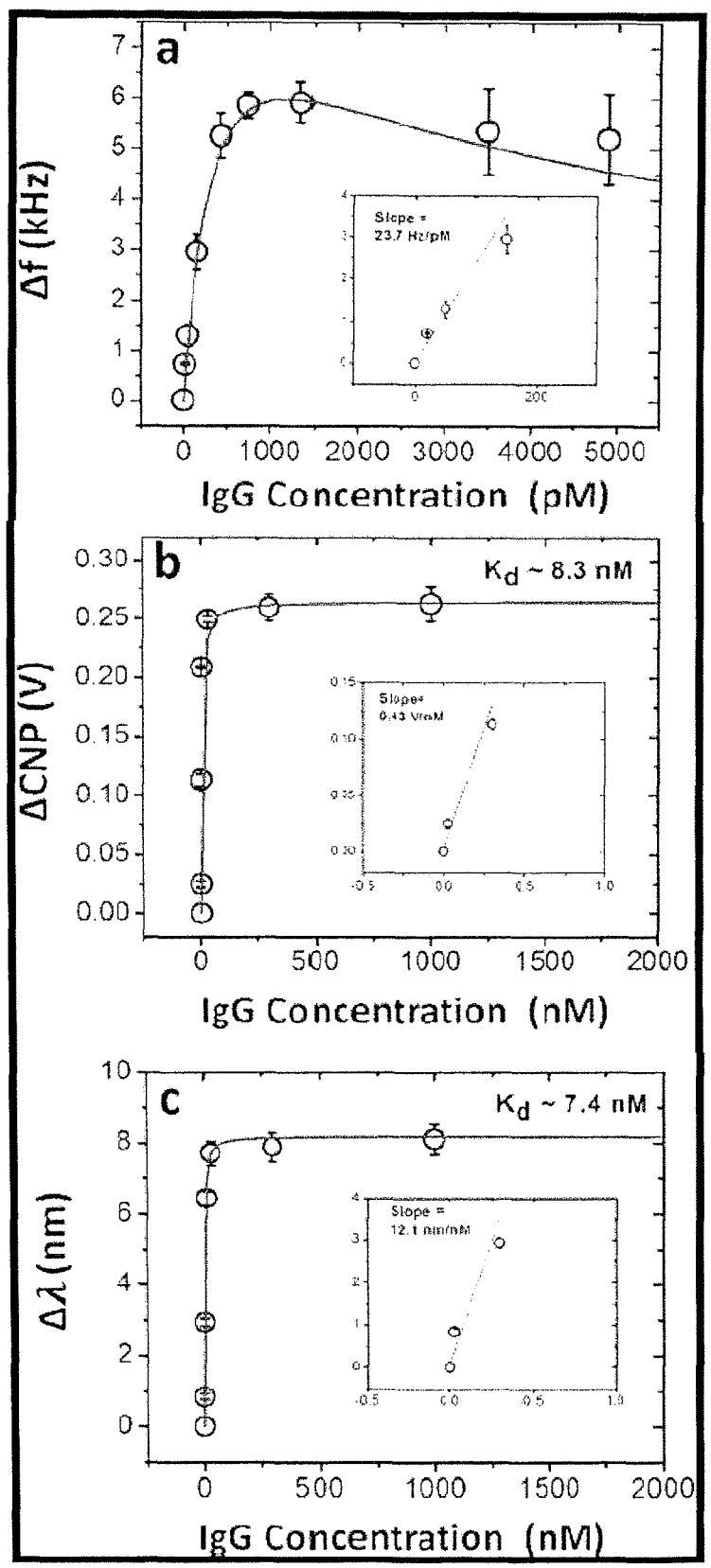
FIG. 3 illustrates Langmuir adsorption isotherms for A/G-IgG device response after functionalizing with protein A/G, as a function of added IgG, in accordance with aspects of the present invention. Panels (b,c) were averaged over six samples and fitted with Equation 1 while panel (a) was averaged over three samples and fitted with Equation 2. Two devices were common to all three sets of measurements. Error bars indicate one standard deviation. Inset: Linear fit to the first few data points of each sensing mode, before significant saturation (deviation of slope of more than 10%) of the response occurs. The sensitivity is defined as the slope of this linear fit, which captures the initial response of the nanosensor. The individual linear dynamic range (defined from minimum detectable concentration to the concentration closest to the turning point of the respective response curves) is approximately 0.5 pM to 1 nM for the mechanical sensing mode and approximately 30 pM to 30 nM for both electrical and optical modes, yielding a combined linear dynamic range from subpicomolar to tens of nanomolar.

In general these values are comparable with their state-of-the-art, single mode counterparts of similar structure and design. More importantly, the overall linear dynamic range (defined from the minimum detectable concentration of the overall device, to the concentration closest to the turning point of the response curves as shown in FIG. 3) is also five orders of magnitude. This is two to three orders of magnitude higher than what most traditional single mode devices or any individual sensing mode on the device of the present invention can achieve, by virtue of the distinct (but overlapping) target concentration regimes of the individual sensing modalities. For example, the individual linear dynamic range is approximately 0.5 pM to 1 nM for the mechanical sensing mode and approximately 30 pM to 30 nM for both electrical and optical modes, yielding a combined range from subpicomolar to tens of nanomolar.

In order to be able to quantify the concentration of analyte present by looking at the sensor response, an analytical relation between the two needs to be established. FIG. 3 reveals qualitatively different sensing responses: the optical and electrical responses (FIG. 3b,c) are seen to plateau and effectively saturate at about 10 nM concentrations, while the mass response (FIG. 3a) peaks approximately an order of magnitude earlier and subsequently decreases. It is believed that this behavior arises as the responses are due to fundamentally different mechanisms: optical and electrical responses are due to local permittivity perturbations and graphene doping, respectively, which scale with fractional protein surface coverage and is well-described by the Langmuir adsorption isotherm yielded $$\Delta = \frac{\Delta_{max}[C]}{K_d + [C]} \quad (4)$$

(Equation 4) where $\Delta$ is the instantaneous response, $\Delta$max is the saturation response, $[C]$ is the protein concentration, and $K_d$ is the Langmuir equilibrium constant of dissociation. Notably, $K_d = (k_{off}/k_{on})$ characterizes the strength of the binding event and is an indication of the surface affinity between the binding surface (here, the graphene) and adsorbate and is equivalent to the ratio of the (dynamic) rates of desorption ($k_{off}$) and adsorption ($k_{on}$). It ought to be emphasized that although the measurements are serial, the long incubation times and subsequent quick postincubation washes of the spotting process (as described herein) ensures that local equilibration of the protein molecules with the sensor surface is achieved during incubation and "frozen-in" after the wash; the measurements can thus be understood as taking a snapshot of an otherwise real-time sensing trial, and the data are expected to follow the Langmuir isotherm. In addition, the applicants observed that the fitted values of $K_d$ for optical and electrical measurements agree well with each other (FIG. 2e,f). These values are also in agreement with other reported values in the literature for conjugated molecular binding. In contrast, therefore, the mass response cannot be saturated at subnanomolar concentrations. The peak and subsequent decrease must thus arise due to the physics of the mechanical resonance itself. Rewriting Equation 1 in terms of the concentration of adsorbates, the applicants obtained $$\Delta f \approx \frac{\kappa}{4\pi} \frac{[C]}{\left[\frac{\beta_1 K_d m_\Omega}{\beta_2 A \Gamma_{max} M_r} + [C]\right]^{3/2}} = \frac{\kappa}{4\pi} \frac{[C]}{\left[\frac{\beta_1 m_\Omega}{\beta_2 \alpha M_r} + [C]\right]^{3/2}} \quad (5)$$

(Equation 5) where $m_\Omega$ is the original bulk mass of the membrane resonator, $K_d$ is the Langmuir equilibrium dissociation constant as defined in Equation 4, $\Gamma_{max}$ is the number of binding sites (in moles per unit area), A the effective surface area of the sensor, $\beta_1$ and $\beta_2$ are the constant modifiers to the membrane and added masses respectively, based on the mode profile of the measured resonance (here, the fundamental mechanical resonance), $M_r$ is the molar mass of adsorbents, and $\kappa$ is a phenomenological constant, taking into account initial stresses or deflections of the membrane. This equation can be derived from the standard equation of a resonator, without neglecting any higher order terms. Also $\beta_1 = \beta_2$ under the assumption that the adsorbed masses possess a spatially homogeneous distribution, that is, there are no local stress centers. In addition, we can define a quantity $\alpha = (A\Gamma_{max}/K_d)$ which is determined exclusively by the nature of the sensor and type of adsorbate, which characterizes the effective "strength" of an interaction. Equation 5 accurately predicts the appearance of a local maximum in the mass response if a is large, or an essentially constant line if a is small, resulting in a highly similar visual appearance to the Langmuir adsorption isotherm.

As a demonstration of a device of the present invention for protein differentiation purposes, two different proteins were characterized, murine IgG and oxidized cytochrome-c (Cyt C) from equine heart, in the optoelectromechanical 3D parameter space (FIG. 4a-d). No intermediary binding protein was used, that is, no specific molecular conjugation in order to extract intrinsic properties of the proteins when adsorbed directly onto graphene. Consequently $K_d$ for IgG increased to 154 nM from 7.4 nM (FIG. 4a) and 171 nM from 8.3 nM (FIG. 4b) for optical and electrical measurements respectively, indicating a much weaker surface binding affinity between the protein and graphene. Cyt C on the other hand is found to possess a fairly low $K_d$ of approximately 9 nM, only marginally weaker than the A/G-IgG binding strength.

Results from the mass sensing component for IgG and Cyt C (FIG. 4c,d) corroborate the optical and electrical results. Using Equation 2, the relevant fitting parameter for mass responses is the quantity $(m_\Omega/\alpha M_r)$ that is found to be about $1.25 \times 10^{-5}$ and $9.05 \times 10^{-5}$ mol dm$^{-3}$ for IgG and Cyt C, respectively. This implies a difference in a (and hence $K_d$, assuming that the number of available sites do not significantly vary for the same device) of about 25 times, taking into account their respective molar masses of 160 and 12 kg. This is consistent with the ratio of $K_d$ of the two proteins (approximately 20 times) obtained from the unconjugated graphene binding experiments in the optical and electrical modes as described previously; differences likely arise because $K_d$ by definition assumes ideal equilibration between the protein and the surface, whereas practically the equilibration process is subject to environmental factors such as pH fluctuations and variations in surface hydrophobicity. The measured affinities of A/G-murine IgG binding as presented herein, characterized by the Langmuir dissociation constant, are in excellent agreement with protein-receptor binding values in the existing literature. As mentioned herein, both the binding affinities and the saturation responses of IgG and Cyt C can be understood by considering their chemical structure and the subsequent interaction with graphene.

The oxidized Cyt C molecule is essentially an $Fe^{3+}$ ion complex surrounded by a highly conjugated porphyrin ring. Because of the innate conjugation and the small size of the molecule, the electron orbitals in Cyt C are able to readily and significantly overlap with the extended n-orbitals of graphene. The $Fe^{3+}$ ion further contributes to this as its valence electrons occupy the highly penetrating 3d sub-shells. This results in a comparatively strong attraction to the graphene surface, as borne out by extensive theoretical studies using ab initio and density functional theory (DFT) calculations of similar phenomena. In contrast, IgG being a massive chain molecule exhibits no such preferential bonding and orbital overlap; its Y-shaped geometry and size (about 10 times greater than Cyt C) are further likely to cause steric hindrance to subsequent molecules that attempt to bind to neighboring sites. Thus, the only factors that lower adsorption energy are inductive effects due to the large and therefore relatively polarizable electron cloud. As a result, the clear discrepancy in binding strengths to graphene, as shown in FIG. 4a-d, was observed.

Figure 4:
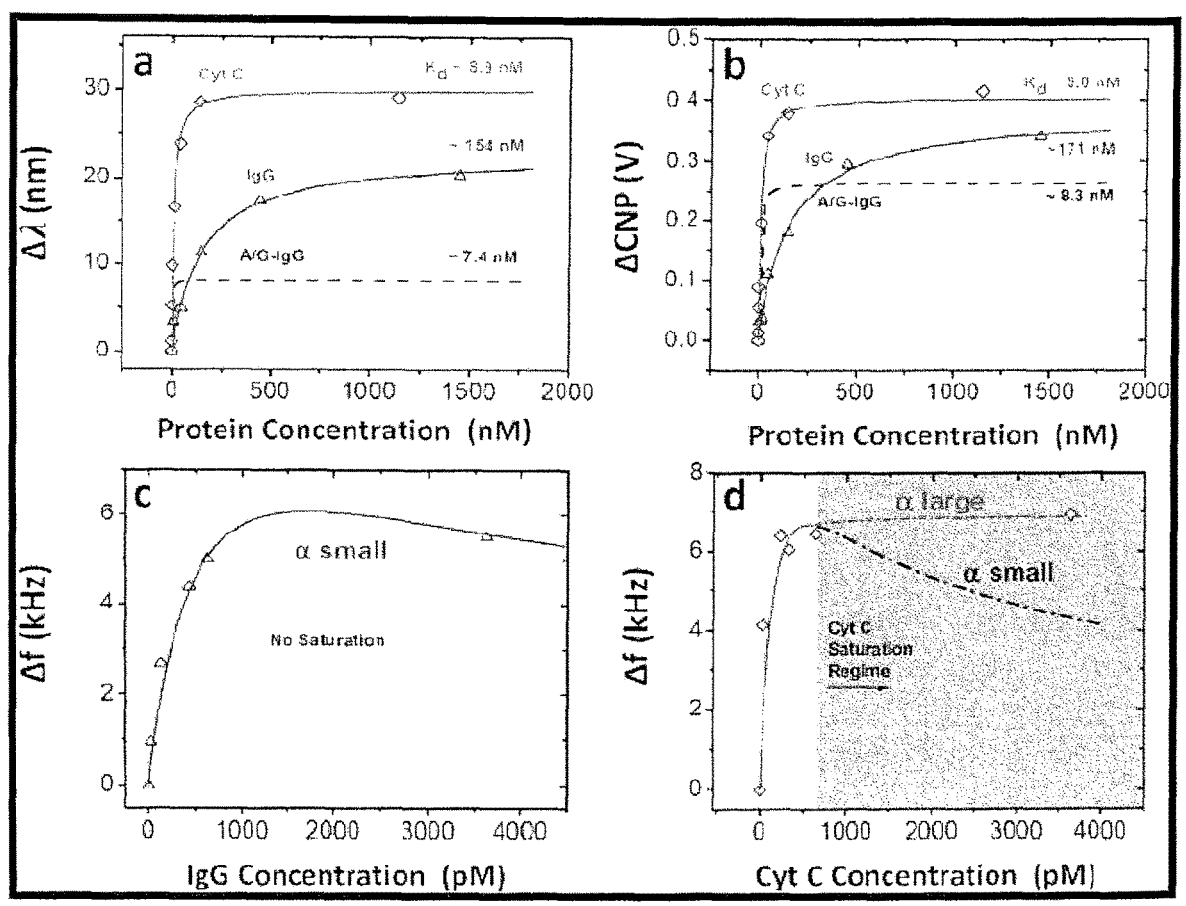
FIG. 4 illustrates unconjugated IgG and Cyt C characterizations. Optical (a) and electrical (b) characterization curves on separate devices without A/G functionalization are shown. Previous A/G-IgG results are shown in black dotted lines. Mass characterizations of unconjugated IgG (c) and Cyt C (d) are shown. Saturation of graphene surface during Cyt C addition is shown by shaded region, resulting in a large a (as defined in Equation 5) and hence apparent "saturation" of the mass response.

The difference in binding strengths give rise to the qualitatively different behavior under mass testing, as discussed herein. It is interesting to consider what gives rise to the difference in saturation response for the optical and electrical sensing modes (FIG. 4a,b). Optically, the resonance peak shift is determined by both the magnitude of the local index change and the volume degree of interaction with the plasmonically enhanced near field. Cyt C has a larger refractive index of about 1.6 but a much smaller size compared to IgG (refractive index~1.3). While it is not immediately clear a priori which molecule would have the larger shift as quantitative information regarding field mode volume of our fabricated structures is unknown, we can certainly rationalize the (optical) experimental results (FIG. 4a); the mode confinement of the gold nanodisk antenna was such that the greater interaction length with IgG dominates. One can expect that for more confined fields, such as those occurring in higher order multipole resonances, the situation may be reversed. Similarly, we can attribute the higher saturation electrical response to the larger number of Cyt C molecules adsorbed; though the relatively significant orbital overlap with graphene enables direct charge transfer from graphene to the oxidized Cyt C molecule, the capacitive gating effect due to IgG is apparently greater per unit mass adsorbed.

By being able to obtain consistent data in all three sensing modes from individual protein additions, unique parameters were extracted, such as binding and dissociation constants, optical and electrical surface sensitivities, as well as saturation responses for IgG and Cyt C molecules. Though in this case these molecules were distinct in terms of mass, molecular size, refractive index, and electronic charge, it follows that one would be able to categorically differentiate between (unconjugated) molecules which are similar in one or more aspects (but not all three). This could also potentially form the basis for a unique protein identification scheme, through the establishment of a library of such data.

An additional experiment was conducted emulating the case where a single mode mass sensor would fail in a complex biomolecular mixture containing two distinct proteins that generated the same mass perturbations (to within error). Pseudorandom, sequential spotting of IgG and Cyt C onto the same samples was performed, with concentrations chosen such that the total adsorbed mass for each type of molecule was the same, that is, they resulted in similar mechanical shifts (with an averaged difference of about 14%) of the membrane resonator. Clearly, the addition of approximately the same mass of Cyt C produced no significant sensor response (below the noise level) in the electrical and optical modes compared to IgG; the signal contrast is an order of magnitude different for the two types of molecules. These results are also consistent with the characterization data shown in FIG. 3, where the larger saturation responses of Cyt C are primarily due to its significantly larger binding constant.

The embodiments described herein are intended to be exemplary of the invention and not limitations thereof. One skilled in the art will appreciate that modifications to the embodiments and examples of the present disclosure may be made without departing from the scope of the present disclosure.

What is claimed is:

1. A multimodal biosensor device, comprising:
a sample analysis region that presents at least a first sensor and a second sensor for exposure to a sample,
the first sensor being of a first sensor type selected from the list consisting of the following three sensor types and the second sensor being of a second sensor type selected from the list consisting of the following three sensor types, the second sensor type being different from the first sensor type:
(i) a nanomechanical resonator;
(ii) plasmonic nanodisk antennae; and
(iii) a field effect transistor,
and
wherein the biosensor device is capable of simultaneously transducing adsorption of biomolecules onto the biosensor device into optical, electrical and mechanical signals.

2. The multimodal biosensor device of claim 1, wherein one of the first sensor and the second sensor comprises a nanomechanical resonator.

3. The multimodal biosensor device of claim 2, wherein the nanomechanical resonator comprises a silicon nitride membrane coupled to a silicon frame.

4. The multimodal biosensor device of claim 3, comprising a metal layer disposed on a surface of the silicon nitride membrane.

5. The multimodal biosensor device of claim 4, wherein the metal layer has a thickness of about 100 nm.

6. The multimodal biosensor device of claim 4, wherein the metal layer comprises silver.

7. The multimodal biosensor device of claim 1, wherein one of the first sensor and the second sensor comprises plasmonic nanodisk antennae, wherein the plasmonic nanodisk antennae comprise gold nanodisk antennae.

8. The multimodal biosensor device of claim 1, wherein one of the first sensor and the second sensor comprises a field effect transistor, wherein the field effect transistor is graphene-based.

9. The multimodal biosensor device of claim 8, wherein the field effect transistor comprises a graphene monolayer.

10. A multimodal biosensor device, comprising:
a sample analysis region that presents at least a first sensor and a second sensor for exposure to a sample,
wherein (i) the first sensor comprises a nanomechanical resonator;
(ii) the second sensor comprises plasmonic nanodisk antennae, wherein the plasmonic nanodisk antennae are disposed on a surface of the nanomechanical resonator substrate; and
(iii) the multimodal biosensor device further comprises a field effect transistor, wherein the field effect transistor is disposed on a surface of the nanomechanical resonator substrate.

11. A method of using a multimodal biosensor device, the method comprising: adsorbing biomolecules onto the multimodal biosensor device,
the multimodal biosensor device comprising a sample analysis region that presents at least a first sensor and a second sensor for exposure to a sample,
the first sensor being of a first sensor type selected from the list consisting of the following three sensor types and the second sensor being of a second sensor type selected from the list consisting of the following three sensor types, the second sensor type being different from the first sensor type:
(i) a nanomechanical resonator;
(ii) plasmonic nanodisk antennae; and
(iii) a field effect transistor, wherein the biosensor device is capable of simultaneously transducing the adsorption of biomolecules onto the biosensor device into optical, electrical, and mechanical signals, and wherein the multimodal biosensor device transduces the adsorption of the biomolecules into an optical signal from plasmonic nanodisk antennae, an electrical signal from a field effect transistor, and a mechanical signal from a nanomechanical resonator; and detecting and differentiating a plurality of different biomolecules adsorbed onto the multimodal biosensor device.

12. The method according to claim 11, wherein the biomolecules are proteins.

13. A method of making a multimodal biosensor device that includes a sample analysis region that presents at least a first sensor and a second sensor for exposure to a sample, the first sensor being of a first sensor type selected from the list consisting of the following three sensor types and the second sensor being of a second sensor type selected from the list consisting of the following three sensor types, the second sensor type being different from the first sensor type: (i) a nanomechanical resonator;
(ii) plasmonic nanodisk antennae; and (iii) a field effect transistor, and wherein the biosensor device is capable of simultaneously transducing adsorption of biomolecules onto the biosensor device into optical, electrical and mechanical signals, the method comprising:
depositing plasmonic nanodisk antennae and a field effect transistor on a top surface of a nanomechanical resonator.

14. The method of claim 13, wherein the nanomechanical resonator is a silicon nitride membrane.

15. The method of claim 13, wherein the plasmonic nanodisk antennae comprise gold nanodisk antennae.

16. The method of claim 13, wherein the field effect transistor is graphene.

17. The method of claim 13 further comprising depositing silver onto a surface of the nanomechanical resonator.

18. The method of claim 13, wherein the nanomechanical resonator is a silicon nitride membrane deposited on a silicon frame, the plasmonic nanodisk antennae comprise gold nanodisk antennae, and the field effect transistor is graphene, the method comprising:
providing the silicon nitride membrane deposited on the silicon frame;
depositing the gold nanodisk antennae, surface source electrodes, and drain electrodes on the silicon nitride membrane by spin-coating a polymethyl methacrylate (PMMA) 495/950 resist bilayer followed by electron beam lithography;
depositing Ti/Au on the silicon nitride membrane using an electron beam evaporator;
depositing silver (Ag) on an underside of the silicon nitride membrane to form a gate electrode;
spin-coating and baking graphene on copper foils with polymethyl methacrylate (PMMA); and
transferring the graphene on copper foils with PMMA onto a field effect transistor channel region of the silicon nitride membrane.

* * * * *